Figure 1:
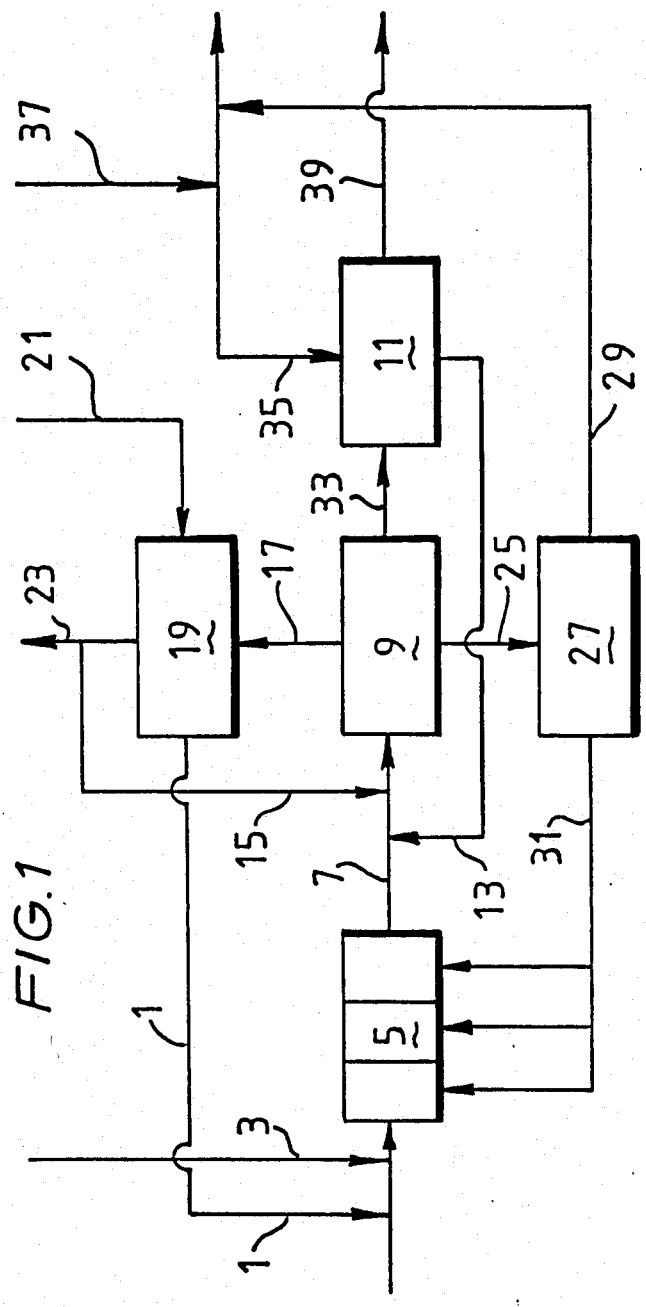

United States Patent [19]

Hanin

[11] Patent Number: 4,625,067

[45] Date of Patent: Nov. 25, 1986

[54] HYDROFORMYLATION CATALYST REMOVAL

[75] Inventor: Jean A. A. Hanin, Rixensart, Belgium

[73] Assignee: Exxon Research & Engineering Co., Florham Park, N.J.

[21] Appl. No.: 803,087

[22] Filed: Nov. 27, 1985

[30] Foreign Application Priority Data

Nov. 30, 1984 [GB] United Kingdom ............... 8430225

[51] Int. Cl.$^4$ .................................................. C07C 45/50
[52] U.S. Cl. ..................................... 568/451; 568/909
[58] Field of Search ..................... 568/451, 454, 909

[56] References Cited

U.S. PATENT DOCUMENTS

| | | | |
|---|---|---|---|
| 2,595,096 | 4/1952 | Parker | 568/451 |
| 2,757,203 | 7/1956 | Hale | 568/451 |
| 2,757,204 | 7/1956 | Ratcliff | 568/451 |
| 2,779,794 | 1/1957 | Catterall | 568/451 |
| 2,779,796 | 1/1957 | Munger | 568/451 |
| 2,905,716 | 9/1959 | Buchner et al. | 568/451 |
| 3,092,670 | 6/1963 | Gwynn et al. | 568/451 |
| 3,196,171 | 7/1965 | Gunter et al. | 568/451 |
| 3,868,422 | 2/1975 | Hart et al. | 568/451 |

FOREIGN PATENT DOCUMENTS

| | | | |
|---|---|---|---|
| 667824 | 3/1952 | United Kingdom | 568/451 |
| 690977 | 4/1953 | United Kingdom | 568/451 |
| 702950 | 1/1954 | United Kingdom | 568/451 |
| 893524 | 4/1962 | United Kingdom | 568/451 |
| 742879 | 1/1965 | United Kingdom | 568/451 |

Primary Examiner—Werren B. Lone
Attorney, Agent, or Firm—J. B. Murray, Jr.

[57] ABSTRACT

Cobalt values are removed from the crude product of a cobalt-catalyzed hydroformylation reaction by contacting the product with stripping gas to entrain volatile cobalt compounds, in the presence of water or aqueous acid to dissolve cobalt values not so entrained.

22 Claims, 2 Drawing Figures

HYDROFORMYLATION CATALYST REMOVAL

This invention relates to a method of removing dissolved cobalt compounds from the products of a cobalt catalysed hydroformylation reaction, particularly but not exclusively such a method wherein the cobalt can be recycled to the hydroformylation reactor.

Hydroformylation reactions involve the preparation of oxygenated organic compounds by the reaction of carbon monoxide and hydrogen (synthesis gas) with carbon compounds containing olefinic unsaturation. The reaction is performed in the presence of a carbonylation catalyst and results in the formation of a compound, for example an aldehyde, which has one more carbon atom in its molecular structure than the starting olefinic feedstock. By way of example, higher alcohols may be produced in the so-called oxo process by hydroformylation of commercial $C_6$–$C_{12}$ olefin fractions to an aldehyde-containing oxonation product, which on hydrogenation yields respective $C_7$–$C_{13}$ saturated alcohols. The crude product of the hydroformylation reaction will contain catalyst, aldehydes, alcohols, unreacted feed, syn gas and by-products.

Before further processing of the crude product is possible, it is necessary to remove the catalyst therefrom. One conventional method of removing cobalt values from such a crude product is to treat the product with an alkali or acid wash technique; however this uses expensive raw materials and moreover leads to difficulties of finally removing essentially all traces of cobalt from the water wash streams before these may be discharged into water courses. Another such conventional method involves the oxidation of the cobalt catalytic species followed by extraction as a salt in aqueous solution.

It is known to remove volatile cobalt compounds from crude hydroformylation reaction products by stripping them out with a countercurrent of synthesis gas. The cobalt contained in the crude product is in the form of complex compounds of cobalt with carbon monoxide, namely cobalt carbonyls, which are either formed during the principal reaction from the cobalt metal or compound introduced into the hydroformylation reactor, or which are introduced into the reactor directly in the form of carbonyls. These cobalt carbonyls are readily soluble in organic liquids (such as the organic products of the oxo-process) when in the form, for example, of the highly volatile hydrocobaltcarbonyl ($HCo[CO]_4$) or in the form of dicobaltoctacarbonyl $Co_2(CO)_8$ which has a low volatility; however the exact species of the cobalt complex in the crude product depends to large extent upon the temperature and pressure conditions applicable. For example, in the presence of hydrogen, dicobaltoctacarbonyl (which is solid at room temperature) reaches an equilibrium with hydrocobaltcarbonyl (which is gaseous at room temperature) the concentration of dicobaltoctacarbonyl being minimised at high temperatures and high hydrogen partial pressures. At high temperatures and low carbon monoxide partial pressures, however, both of these carbonyls decompose with precipitation of cobalt or cobalt oxide. Hitherto known stripping techniques have had to take account of the equilibria established in the cobalt/carbon monoxide complex system, and accordingly gas stripping techniques using specified conditions have been necessary.

According to GB No. 893 524 (Magyar Asranyolaj es Foldaz Kiserleti Intezet) a crude oxo product is said to be decobalted by stripping volatile cobalt compounds from the crude product, using a mixture of carbon monoxide and hydrogen as the stripping gas. Elevated temperatures of 140–200° C. are employed, and it is required that the hydrogen contained in the stripping gas has a partial pressure which is greater than 10 atmospheres and the carbon monoxide has a partial pressure which is above 10 atmospheres and greater than the decomposition pressure of the cobalt compounds present in the crude product at the temperature employed. The elevated temperatures and pressures (for example 200° C. and 300 atmospheres), are employed to prevent decomposition of the dissolved cobalt compounds to metallic cobalt.

U.S. Pat. No. 3 868 422 (Hart et al) also addresses the problems caused by plating-out of catalyst residue on the pumps and associated lines of hydroformylation reaction systems. To prevent such plate-out and also to provide good catalyst distribution within the hydroformylation reaction system, the reaction is performed in a multistage reactor at elevated temperature and pressure, with introduction of synthesis gas into the final reactor stage in countercurrent to the crude product. The synthesis gas is at elevated temperature and pressure (100°–200° C., 1000–6000 psi) and serves to entrain the volatile cobalt compounds present in the crude product and carry these back into the reaction zones.

U.S. Pat. No. 2 595 096 (Parker) actually makes use of the plating out of the cobalt as a means of removing cobalt from the system. Thus in a catalyst removal zone at 200°–450° F. which may be packed with an inert solid material, crude oxo-product is treated with a countercurrent of hydrogen-containing gases which carry off carbon monoxide from decomposing cobalt carbonyls, leaving cobalt metal to deposit on the packing or walls of the removal zone.

GB No. 667 824 (NV de Bataafsche Petroleum Maatschappij) uses a gas comprising hydrogen and carbon monoxide to decobalt aldehyde-containing crude oxo-product at high temperatures (eg 150°–250° C.) and pressures of preferably 25–50 atm, the carbon monoxide serving to prevent simultaneous reduction of the aldehyde. These conditions decompose the cobalt catalyst present, leading to deposition of cobalt metal on pumice pieces contained in the decobaltation pressure vessel. The deposited cobalt has to be removed from time to time.

U.S. Pat. No. 2 757 203 (Hale) is primarily concerned with treatment of the crude oxo-product with steam in the presence of acid, but such conditions are said to result in the bulk of the cobalt carbonyl present being decomposed to the metal and carbon monoxide. There is no suggestion to employ conditions such that there is entrainment of cobalt in usable (recyclable) form and dissolution of any cobalt remaining in the organic phase into an aqueous phase.

U.S. Pat. No. 2 905 716 (Buchner et al) purifies metal catalystcontaining aldehyde from the oxo process by treatment with water at 150°–200° C., the metal being converted to precipitated hydroxide, oxide or the metallic state under the conditions employed.

U.S. Pat. No. 3 092 670 (Gwynn et al) delivers crude oxo-product to a demetalling zone packed with an inert material such as pumice, followed by heating directly or indirectly with steam to decompose the metal carbonyl and deposit the free metal on the pumice.

U.S. Pat. No. 2 779 794 (Catterall) is concerned with the decobalting of crude oxo-product streams and provides a good description of the problems associated with plugging of equipment by cobalt deposits. One method known to the author for removing cobalt from such streams is said to be a thermal treatment of the crude product (300°–350° F.) under a pressure of 100–175 psig (maintained eg by added hydrogen gas) in order to keep a low carbon monoxide partial pressure. Under such conditions cobalt deposits are formed in the thermal decobalting unit, which has periodically to be taken off stream for cobalt removal in order to prevent plugging. Such thermal treatment is said to leave 100-500 ppm cobalt in the oxo-product stream. The developments more fully described by Catterall are directed towards what is said to be a more complete removal of cobalt from the crude oxo-product, by decobalting in the presence of 2–50 vol. % water but in the absence of added gases at 250°–500° F. and under a pressure of 50–175 psi. The thermal treatment is continued for a long contact time (0.5-4 hours) and results in the formation of a slurry of cobalt solids suspended in aqueous (formic) solution, which slurry is intermittently or continuously withdrawn for solids recovery. Various recovery and recycle options are outlined, but in all cases it is necessary initially to handle an aqueous slurry rather than an aqueous solution, believed to be because the thermal/aqueous decobalting step is performed on the entire cobalt content of the crude oxo-product, rather than, as is the case with the instant invention, on a product which has had its cobalt content reduced by gas stripping. It is readily recognised that handling of slurries is less convenient than handling of solutions in this context, and moreover that the use of an aqueous/thermal decobalting procedure without added gas does not provide the option of recycling at least a part of the cobalt content of the crude oxo-product via absorption into the olefinic oxo reactor feed.

U.S. Pat. No. 2 779 796 (Munger) is also concerned with the decobalting of crude oxo-product and employs the injection of live steam into such product in order to remove soluble cobalt compounds by decomposition or precipitation whilst at the same time avoiding contact of the crude product with fixed heating surfaces. This technique produces cobalt in solid form, via the known thermal decomposition method, but with heat being introduced by live steam at 212°-400° F., the solids are not deposited on heating surfaces but rather form an aqueous emulsion from which solids are removed by known physical techniques. The live steam introduced to the system is said to result in the precipitation of most of the cobalt in the crude product, an aim which is to be distinguished from the object of the instant invention, wherein the bulk of the cobalt in the crude product is removed by a stripping gas which remains gaseous at low temperatures, e.g. below 100° C., with the balance being solubilized in an aqueous phase rather than depositing as a solid.

GB No. 742879 (Esso Research and Engineering Company) employs aqueous organic acid solution at elevated temperature as the treatment medium for soaking crude oxo product in which cobalt catalyst species are dissolved. A pressure of carbon monoxide and hydrogen in excess of of 10 psi is maintained over the mixture, and the conditions are said to be such that the cobalt in the organic phase is converted to water soluble form. The method described requires a reaction time of for example 30–120 minutes, and it is clear that there is no suggestion to employ the aqueous acid techniques simultaneously with use of a stream of stripping gas to entrain volatile cobalt compounds which may be present in the crude oxo product.

This prior art document makes reference to GB No. 690977, which is concerned with precipitation of cobalt compounds from the crude oxo product by reaction with oxalic acid introduced in the form of a non-aqueous solution. Also referred to is GB No. 702950 which teaches the same use of aqueous organic acid solution on GB No. 742879 for removal of cobalt from the oxo product, but without the requirement to maintain an elevated carbon monoxide and hydrogen pressure over the reaction mixture.

It has now been found that cobalt values may be removed from a crude hydroformylation reaction product without the need for close control of the temperature and pressure conditions employed, and in particular using conveniently low temperatures and pressures, and also without the need to handle inconvenient slurries containing cobalt solids. Thus according to the present invention there is provided a method of removing cobalt values from the crude product of a cobalt-catalysed hydroformylation reaction by contacting the crude product with a stream of stripping gas to entrain volatile cobalt compounds, characterised in that said contacting is performed in the presence of water or aqueous acid to dissolve those cobalt values not entrained in the gas under the conditions of temperature and pressure employed for said contacting, and the aqueous phase is subsequently separated from the organic hydroformylation reaction product.

The stripping gas which is preferably used in accordance with the invention is synthesis gas, that is carbon monoxide and hydrogen mixture, the particular proportions of the two components in the synthesis gas being adjusted to suit the reaction system. The stripping gas may, though, comprise for example nitrogen or a light hydrocarbon such as propane or butane.

It is preferred in accordance with the invention that the volume ratio of stripping gas to crude product at the applied conditions is from 20:1 to 250:1, more preferably 50:1 to 125:1. Of course a higher ratio may be used, with good effect, but high ratios may be detrimental to the economic basis of the process. The limiting lower value of the ratio, it will be appreciated, will be reached when there is insufficient stripping gas flow to achieve the desired degree of cobalt volatiles removal. Similarly any flow rate of stripping gas may be used, sufficient to give the desired entrainment of cobalt volatiles. The liquid (organic plus aqueous) phase is preferably well dispersed to give good contact between the liquids. It is preferred, too, that the stripper unit includes inert solid surfaces or trays to facilitate contact between the liquid and gas phases.

A feature of the invention is that, since the stripping stage is performed in the presence of water or an aqueous acid, it becomes unnecessary to maintain a tight control on the temperature and pressure conditions in order to adjust the dicobaltoctacarbonyl/hydrocobaltcarbonyl equilibrium, so as to prevent the cobalt carbonyl decomposition which leads to deposition of solids. As has been recognised in the prior art, elevated temperatures are conducive to the cobalt being in a volatile form and hence readily removed by entrainment in the stripping gas. Unfortunately, though, under such high temperature conditions an elevated partial pressure of carbon monoxide in the stripping gas is required to prevent excessive decomposition of the cobalt carbonyls and resulting deposition. This gas pressure considerably reduces the volatility of the hydrocobaltcarbonyl to a point where the technique becomes economically unattractive because of the large excess of stripping gas required. At the relatively low temperature and pressure conditions which are more desirable in practice, though, there is a much greater possibility of deposition of cobalt metal or cobalt oxide in the crude organic product. Thus it has been shown that low temperature (less than 100° C., preferably less than 90° C.) low pressure stripping leads to plugging of the equipment by solid cobalt or cobalt-containing substances.

It will be recognised therefore that the present invention permits operation of the decobalting process at the more convenient low temperatures and pressures, when conventionally, plate-out danger is greatest: the necessary presence of water or aqueous acid means that the relatively low concentration of non-volatile cobalt values not removed by stripping (including those formed by virtue of the equilibrium established under the stripping conditions) do not plate-out onto the process equipment, but rather go directly into conveniently handled solution in the aqueous phase, thus avoiding plugging of the stripper unit. Without wishing to be bound by theory, the method may be conceived as one of removing cobalt values by two separate but related techniques carried out simultaneously. Thus a major proportion of the volatile cobalt compounds present in the organic phase is removed by entrainment in the stripping gas; and the remaining cobalt species which were either present initially or are produced by reaction occuring during stripping are dissolved into the aqueous phase and removed from the organic phase by phase separation. The method permits operation at stripping temperatures and pressures which are known in conventional processes to promote deposition of metallic cobalt or solid cobalt species.

In the case where water (rather than aqueous acid) is present, then cobalt may be removed as $Co[Co(CO)_4]_2$ solution. However, such compound cannot readily be concentrated by a flashing technique without danger of cobalt entrainment in the overheads which form part of the hydroformylation process waste streams. A consequence of this difficulty in concentration is that the relatively dilute solutions of $Co[Co(CO)_4]_2$ do not readily lend themselves to a recycle step, ie reintroduction to the oxo reactor. It is thus greatly preferred that the method of the invention is performed in the presence of an aqueous acid, in view of the components present in the crude oxo product. Any suitable acid may be used, for example an inorganic acid such as sulphuric or an organic acid such as acetic or formic acid. For a variety of reasons it is especially preferred that the aqueous phase comprise a dilute formic acid, for example 1-2 wt. % formic acid. Preferably, the water or aqueous acid is present in an amount of from 5-15 wt. % based on the amount of crude product.

As mentioned above, it is preferred to employ an acidic aqueous phase in the method of the invention, and reference is made to the following reaction equations by way of explanation:

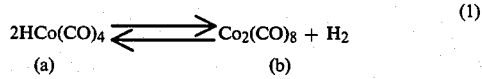
(a)     (b)

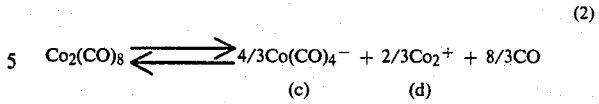
(c)     (d)

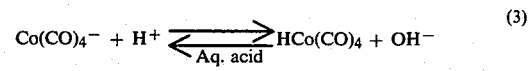

Equilibrium (1) exists in the organic phase, and in use of the method (a) is removed by the stripping gas. Some (b) is also present and under the temperature and pressure conditions employed reacts according to (2) to give (c) and (d) which are preferentially extracted into the aqueous phase. In a neutral environment (c) and (d) remain in the aqueous phase and may be removed from the system as $Co[Co(CO)_4]_2$. In an aqueous acidic environment, however, (described here with reference to formic acid), equilibrium scheme (3) applies. Thus the acid proton combines with (c) to form the more volatile (a) in the aqueous phase, and this is removed by means of the stripping gas directly from the aqueous phase or following its extraction into the organic phase. The acid anion (formate) functions to solubilise the $Co^{2+}$ cation (d) in the aqueous phase as cobalt formate solution. Thus the concentration of hydrocobaltcarbonyl present in the aqueous phase (as hydrocobaltcarbonyl (a) per se or as its anion (c)) is advantageously reduced when the aqueous phase is acidic; the amount of volatile cobalt remaining in the aqueous phase (and in the organic phase) is decreased to minimal amounts. It is particularly preferred to use formic acid as the aqueous phase reouired to be present in accordance with the invention, since formic acid is one of the organic compounds produced in the hydroformylation reaction and its associated secondary reactions to which this invention relates. Hence after an initial introduction of formic acid it is possible by using the recycle option described herein to make the system substantially closed with regard to formic acid.

The present invention permits decobalting at relatively low pressures, and preferably the method is conducted at pressures lower than the decomposition pressure of the cobalt compounds present in the crude hydroformylation reaction product at the temperature conditions employed. More preferably the pressure is below 20 atmospheres, most preferably below 10 atmospheres, especially for example a low pressure below 7 atmospheres such as from 1-5 atmospheres. The temperature employed generally relates to the pressure and is preferably less than or no more than 100° C. or 90° C., more preferably from 60-100° C., especially 60 to 80, 85 or 90° C. Generally temperatures of less than 80° C. are advantageously used.

It will be appreciated that the defined decobalting method may be employed as a process step in an oxo process comprising hydroformylating an olefinic feedstock with synthesis gas in the presence of a cobaltcontaining catalyst to form a product mixture containing higher aldehyde, alcohol, unreacted feed and secondary products. The decobalting method is employed prior to further treatment of the product mixture.

In accordance with the present invention, after contacting the crude product with the stripping gas, the cobalt-containing aqueous phase is separated from the treated product. Preferably this aqueous phase is concentrated, and the concentrate, for example containing from 1-2 wt. % cobalt (as metal) may be introduced into the hydroformylation reaction zone. The maximum amount of cobalt in the concentrate depends on the solubility in water of the cobalt compound in question, which itself is temperature dependent. Preferably the concentrate contains the maximum possible amount of solubilised cobalt for the particular operating temperature. The concentrate may be produced by flashing the aqueous phase in an evaporator or by using any other convenient means such as a membrane, to yield the concentrate, for example a cobalt formate/formic acid aqueous solution, and substantially pure water which may be purged from the system.

In order to ensure that such purged water is environmentally clean, ie contains less than 10 ppm cobalt, it is prefered to subject the cobalt-containing aqueous phase to oxidation, for example by injection of a molecular oxygen-containing gas such as air into the line from the stripping unit. This serves to destroy traces of volatile carbonyl compounds which may not have been entrained by the stripping gas. Such traces would otherwise be removed with the "pure" water overheads in the flashing unit, causing downstream contamination problems.

Recycle of the aqueous concentrate to the hydroformylation reaction ensures that catalyst concentration in the reaction zone is maintained, since under the oxonation conditions the cobalt in the concentrate converts to the active catalytic species useful in hydroformylation. In addition, such recycle serves to maintain the presence of water or aqueous acid in the crude product, in accordance with the invention. However, such concentrate recycle is preferably not practised when the aqueous phase comprises an inorganic acid such as sulphuric, since this has been found to increase the make of undesired byproducts. As mentioned, the cobalt concentration in the hydroformylation reaction zone may also be, and preferably is, maintained by dissolving volatile cobalt compounds entrained in the stripping gas in a countercurrent of the olefinic feed to the hydroformylation reaction zone. The thus treated stripping gas can then either be purged or recycled for further contact with the crude product. It will be appreciated therefore that synthesis gas is the preferred stripping gas, since its subsequent recycle contact with the olefinic feedstock will not cause the introduction of undesirable materials into the subsequent oxonation reactor. Under the conditions employed substantially no water will be carried over by the stripping gas (synthesis gas) and introduced into the olefin feed. If necessary the cobalt-containing stripping gas may be cooled prior to contact with the feed, and condensed water refluxed into the stripper.

With regard to the concentrate obtained from the aqueous phase of the method of the invention, this may, instead of recycle to the hydroformylation reaction, be purged and the cobalt recovered as for example cobalt oleate. This is preferred where the concentrate comprises an inorganic acid.

In some systems, it is preferred not to recycle the aqueous cobalt concentrate to the hydroformylation reactor. For example, where the reactor is liable to corrosion problems such recycle would not be desirable. A further option open to the operator of the method according to the invention is therefore to deliver the concentrate to a cobalt preformer unit. Conventionally such units are employed to produce cobalt in a form suitable for injection into the oxo-reactor, for example as a slurry of cobalt oxide, $Co_3O_4$, in higher alcohol or as a solution of cobalt soap, e.g. decanoate, oleate or naphthenate in higher alcohol. In a preferred embodiment of the invention the concentrate, especially when not based on an inorganic acid, is introduced into the cobalt preformer, and the resulting mixture is injected into the crude oxo product downstream of the oxo reactor but upstream of the stripper unit, or directly into the stripper unit. Here the stripping gas carries off the volatile cobalt carbonyls present (including those newly introduced to the system from the cobalt preformer) and, via extraction into the olefin feed, into the oxo reactor. By such an embodiment only minimal quantities of fresh cobalt need be introduced into the cobalt preformer, as make up for an otherwise closed system.

It has been found that during performance of an oxo process using the stripper gas technique described, but without water or aqueous acid present, some 60-80 wt. % of the cobalt contained in the crude oxo product can be recovered from the stripper gas. The remaining 20-40 wt. % of cobalt remains in the oxo product and may lead to plate-out in the stripper unit or downstream, causing plugging. Introduction of, for example, 5-15 wt. % water or dilute acid, preferably formic, into the crude oxo product results in some 66-90 wt. % of the cobalt being removed in the stripping gas with substantially all the balance of 10-34% of cobalt being separated from the oxo product in the stripper as cobalt salt, preferably formate, aqueous solution. The treated crude product will still contain a low proportion of cobalt, for example less than 100 ppm, and this may be removed by a downstream water wash technique yielding an acceptable crude product which contains less than 10 ppm cobalt. The water wash product of the downstream washing stage may if desired be introduced into the crude hydroformylation reaction product prior to contacting with stripping gas. Indeed this may be used to complete a closed system whereby after initial introduction of water or aqueous acid, the system enters a closed loop and substantially no further injection of water or aqueous acid or catalyst (other than minimal make up quantities) is required.

In a particularly preferred embodiment stripping is performed at about 95°C. or below and about 1 atmosphere gauge pressure, using synthesis gas as the stripping gas, in a volume ratio of about 100:1 compared with the crude oxo product. The syn gas with entrained cobalt carbonyls is passed in countercurrent with olefin feedstock which is then delivered to the hydroformylation reactor. The preferably acidic aqueous phase from the stripper unit is concentrated and recycled to the hydroformylation unit or a catalyst preformer, and the treated crude product is subjected downstream to a secondary water wash, the aqueous product thereof, or at least a proportion, being injected into the crude hydroformylation product before or in the stripper unit. Such a system is substantially closed, and has been found generally to give no precipitation of cobalt or cobalt oxide, the unstripped cobalt instead being separated in the form of a salt which can be recycled; the catalyst cycle thus requires substantially no input of chemicals, and the system is environmentally clean.

Figure 2:
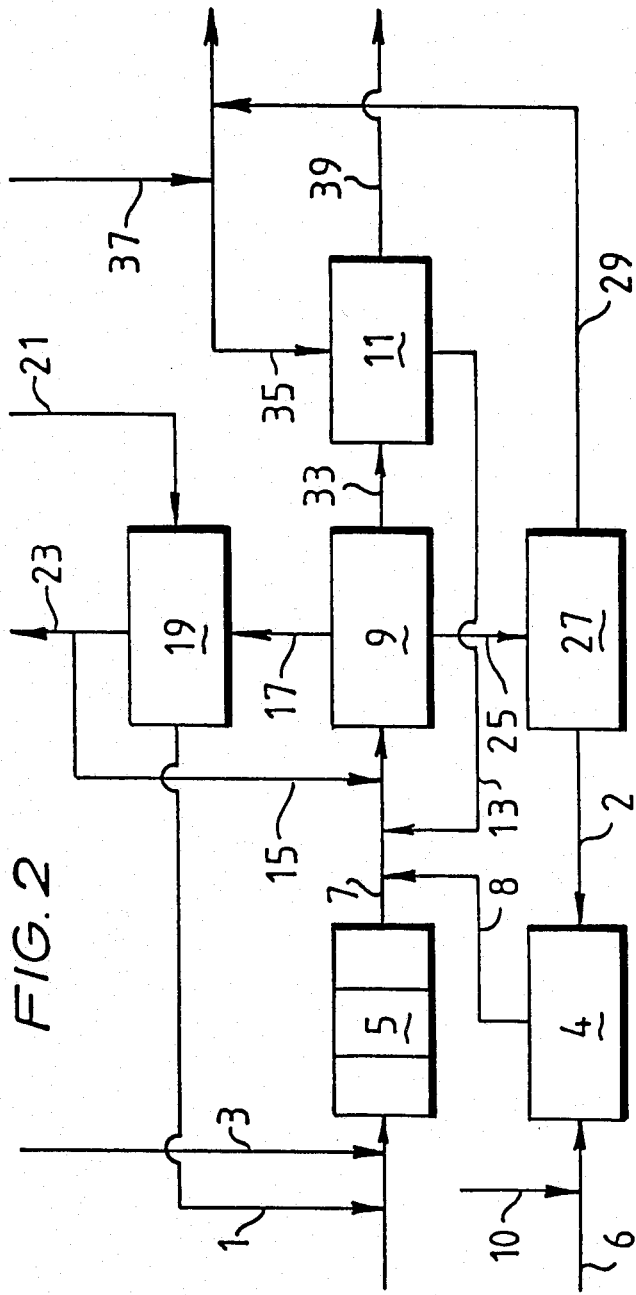

For a better understanding of the invention and to show how the same may be carried into effect, reference is now made, by way of example, to the accompanying drawings, in which;

FIG. 1 is a flow diagram of a hydroformylation reaction system embodying the process of the invention; and FIG. 2 is a flow diagram of the system of FIG. 1 but adapted to avoid recycle of cobalt concentrate direct to the oxo-reactor.

Referring to FIG. 1, feed olefin and syn gas are delivered in desired ratio via respective lines 1 and 3 to an oxo-reactor 5, wherein hydroformylation is conducted under conventional conditions to yield a crude hydroformylation product containing aldehydes, alcohols, by products and cobalt catalyst compounds. This crude product is carried via line 7 to a stripper unit 9, and also introduced into the stripper unit is water from a wash tower 11 via line 13 and stripper gas via line 15. The stripper gas may be for example syn gas or nitrogen. In the stripper unit the stripper gas contacts the crude hydroformylation product and entrains much of the volatile cobalt carbonyl compounds contained therein, carrying them off via line 17 to absorber unit 19. Here the cobalt-containing stripper gas is run in counter current to a supply of feed olefin delivered from line 21 and by virtue of its good solubility in the organic phase the volatile cobalt becomes absorbed in the olefin and carried via line 1 to the oxo-reactor. The feed introduced into the reactor therefore contains cobalt, effecting recycle of at least part of the cobalt catalyst used in the hydroformylation reaction. The stripping gas leaving the absorber 19 may be purged via line 23 or recycled to the stripper unit 9 via line 15. By virtue of the water introduced into the stripper unit via line 13, stripping is conducted in the presence of an aqueous phase, into which dissolves the cobalt species not entrained by the stripping gas. Such aqueous phase is removed from the stripper 9 via line 25, into which air is optionally injected to oxidise any volatile cobalt carbonyls contained therein. The cobalt-containing aqueous phase is subjected to concentration in flash unit 27, with environmentally clean (<10 ppm cobalt) water being removed overhead and purged via line 29. The cobalt-containing concentrate is removed from the flash unit and recycled to oxoreactor 5 via line 31. Thus the loss of cobalt from the system is minimised and water employed in the stripper unit in accordance with the invention is returned to it via the oxo-reactor. Optionally a cobalt make up line to the oxo-reactor (not shown) may be included.

The crude oxo product, having had substantially all its cobalt content removed in stripper unit 9 is carried therefrom via line 33 to the wash tower 11, where water introduced via line 35 (which may be make up water from line 37 or recycled clean flash unit water from line 29) is used in a conventional step for finally removing the remaining cobalt catalyst content of the oxo-product. In the embodiment shown, such wash water is returned to the stripper via line 13. The thus decobalted oxo-product is carried via line 39 to further process stages such as distillation or hydrogenation.

Since formic acid is produced during the oxo-reaction, even if pure water is employed originally, the closed system described soon stabilises into a closed formic acid system, with the advantages described hereinbefore. Optionally, formic acid may be introduced into the system initially at any convenient point.

Referring now to FIG. 2, the embodiment shown is identical with that shown in FIG. 1, save for the manner in which the cobalt concentrate leaving the flash unit 27 is handled. Instead of being carried direct to the oxo-reactor, the concentrate is delivered via line 2 to a cobalt catalyst preformer unit 4. Also delivered to this preformer unit 4 via line 6 is a supply of cobalt to make up for the small amounts inevitably lost in the system. The make up may take the form for example of a slurry of cobalt oxide in higher alcohol (preferably the product of the oxo-reaction) or a solution of cobalt soap in higher alcohol. In the preformer unit the cobalt-containing materials are mixed and volatile cobalt carbonyls are carried via line 8 to the oxo output line 7 by means of a flow of gas, preferably syn gas, injected into the unit via line 10. The cobalt catalyst then becomes entrained in the stripper and thus recycled to the oxo-reactor via the olefin feed, without any direct introduction of an aqueous cobalt concentrate into the oxo-reactor.

The following examples illustrate the invention.

EXAMPLE 1

Hydroformylation was performed using a feed comprising (i) syngas containing hydrogen and carbon monoxide in a molar ratio of 1.16:1 and (ii) a commercially available stream of branched nonenes including also about 2 wt. % octenes and about 8 wt. % decenes. The olefin feed was delivered at a rate of 1.5 l/hr (1115 g/hr) and the syngas at a rate of 640 standard l/hr, into three 1.0 litre capacity oxonation reactors arranged in series, and the reaction was carried out at a pressure of 300 atm and a temperature of 175° C., using a cobalt catalyst at 0.3 wt. % based on the feed and delivered to the reactors in the feed. The total oxo product was then rapidly cooled down, and the excess syngas was separated in a short residence separator operated at 300 atm. The oxo product was sent via a heat exchanger to the top of the stripper unit where it was counter currently contacted with syngas injected at the bottom of this unit. The stripper unit employed in this reduced scale apparatus comprised a 100 cm long column of internal diameter 3 cm, packed with stainless steel half cylinders 3 mm in length. Both the stripper inlet temperature and the temperature within the stripper were controlled, and the flow of stripping syngas was monitored. The syngas with entrained cobalt leaving the top of the stripper was sent to an absorber where the volatile cobalt was absorbed into a branched nonenes liquid. The oxo product leaving the bottom of the stripper and the nonenes leaving the absorber were accumulated in respective drums, weighed and analysed for cobalt content. This process was maintained under constant operating conditions for 94 hours until it was halted by stripper plugging. The plugging material was analysed and found to be cobalt formate. The operating conditions and the outlet cobalt distribution are reported in Table 1.

TABLE 1

| STRIPPING CONDITIONS | |
|---|---|
| Temperature | 68° C. |
| Pressure (atm abs) | 1.8 |
| Syngas ratio (1) | 216 |
| OUTLET COBALT DISTRIBUTION (2) | |
| Cobalt absorbed in nonenes (3) | 73.4 |
| Cobalt in oxo product | 18.5 |
| Cobalt deposited in stripper | 9 |
| | 100.9 |

(1) Standard volume of syngas per volume of oxo product.
(2) Percent by weight based on cobalt delivered to oxonation reactors with feed.
(3) Termed the stripped cobalt.

EXAMPLE 2

The hydroformylation and separation of excess syngas was performed in the same equipment and under the same conditions as Example 1. As before, the syngas with entrained cobalt was run to a nonenes absorber where the cobalt was transferred; the nonenes product was collected and analysed. Similarly, the oxo product was delivered to the stripper unit as in Example 1, but in this case water was injected in the oxo product prior to its introduction at the top of the stripper. The oxo product and the water withdrawn from the stripper were separated and each phase was weighed and analysed for cobalt. This test was terminated after 220 hours with no sign of plugging. The results of the test are summarized in Table 2.

TABLE 2

| STRIPPING CONDITIONS | |
|---|---|
| Temperature | 73° C. |
| Pressure (atm abs) | 1.8 |
| Syngas ratio (1) | 115 |
| Water (4) | 5 |
| OUTLET COBALT DISTRIBUTION (2) | |
| Cobalt absorbed in nonene (3) | 65.9 |
| Cobalt in oxo product | 5.4 |
| Cobalt in stripping water | 28.3 |
| | 99.6 |

(1) Standard volume of syngas per volume of oxo product.
(2) Percent by weight based on cobalt delivered to hydroformylation reactors with feed.
(3) Stripped cobalt.
(4) Volume percent based on oxo product.

A sample of the water phase removed from the stripper, containing 4361 ppm of cobalt, was acidified with sulfuric acid and stripped by bubbling nitrogen through at a gas flow rate of 3 l/minute. After 15 minutes the cobalt content had dropped to 2135 ppm and stayed at that level as evidenced by the cobalt content of 2135 ppm after 30 minutes stripping. From this it was deduced that approximately 50 percent of the cobalt contained in be stripper water was in the form of hydrocobalt carbonyl, which is the only cobalt species which can be stripped in this manner.

EXAMPLE 3 A test similar to that described in Example 2 was carried out but instead of water injection into the oxo product, there was injection of a 1 wt. % aqueous solution of sulfuric acid at the top of the stripper unit. The test was terminated after 50 hours with no sign of plugging. Results are summarized in Table 3.

TABLE 3

| STRIPPING CONDITIONS | |
|---|---|
| Temperature | 80° C. |
| Pressure (atm abs) | 1.8 |
| Syngas ratio (1) | 100 |
| Sulfuric acid solution (4) | 8 |
| OUTLET COBALT DISTRIBUTION (2) | |
| Cobalt absorbed in nonenes (3) | 82.1 |
| Cobalt in oxo product | 0.3 |
| Cobalt in stripping water | 16.2 |
| | 99.6 |

(1) Standard volume of syngas per volume of oxo product.
(2) Percent by weight of total cobalt fed to hydroformylation reactor.
(3) Stripped cobalt.
(4) Volume percent based oxo product.

Further stripping with a nitrogen stream of the aqueous phase collected at the bottom of the stripper did not decrease its cobalt content, which remained at 4469 ppm. From this it may be deduced that the aqueous phase did not contain any cobalt in volatile form.

EXAMPLE 4

A test similar to that described in Example 3 was carried out but with injection of a 1.5 wt. % aqueous solution of formic acid at the top of the stripper unit. Furthermore, the oxo product withdrawn from the bottom of the stripper was sent (after separation of the aqueous phase) to a wash tower where it was washed in countercurrent with water (8.7 volume percent based on oxo product). The oxo product after washing was analysed for cobalt content. The wash water was recycled to the top of the stripper and injection of fresh formic acid solution was discontinued. The aqueous phase withdrawn at the bottom of the stripper was evaporated in a flash drum, and the overhead containing no cobalt but containing part of the formic acid was sent to the wash tower and used as washing water. The bottoms of the flash (concentrated in cobalt formate) was recirculated to the first hydroformylation reactor. When necessary, a water make-up was introduced at the wash tower, and the formic acid content of the stripping water was maintained at 1.5 wt. %. The branched nonenes into which the cobalt entrained in the stripping syngas was absorbed was deliver to the oxonation reactor as process feed.

The various streams in this continuous process were analysed periodically. The process was terminted after 229 hours with no sign of plugging. The rest conditions are summarized in Table 4, and the analytical results in Table 5.

TABLE 4

| STRIPPING CONDITIONS | |
|---|---|
| Temperature | 95° C. |
| Pressure (atm abs) | 1.8 |
| Syngas ratio (1) | 111 |
| Formic acid solution (2) | 9.2 |
| WASHING CONDITIONS | |
| Temperature | 60° C. |
| Pressure (atm abs) | 1 |
| Formic acid solution (2) | 8.7 |
| WASHING CONDITIONS | |
| Temperature | 60° C. |
| Pressure (atm abs) | 1 |
| Formic acid solution (2) | 8.7 |
| FLASH CONDITIONS | |
| Bottom temperature | 102° C. |
| Overheads (3) | 68.3 |
| Bottoms (13) | 41.5 |

(1) Standard volume of gas per volume of oxo product.
(2) Volume percent based on oxo product.
(3) Percent by volume of total flash feed.

(2) Volume percent based on oxo product. (3) Percent by volume of total flash feed.

TABLE 5

| COBALT DISTRIBUTION | |
|---|---|
| Cobalt recirculated with nonenes (1) | 81.5 |
| Cobalt recirculated with water (1) | 17.2 |
| Cobalt make-up as dicobaltoctacarbonyl (1) | 1.3 |
| Test cobalt balance (2) | 99.3 |
| COBALT ANALYSIS | |
| Stream | Cobalt Content (3) |
| Oxo product after stripping, before washing | 0.0018 |
| Washed oxo product | none (4) |
| Aqueous phase from wash tower | 0.0234 |
| Flash overheads | none (4) |

TABLE 5-continued

| | |
|---|---|
| Flash bottoms | 1.39 |

(1) As percent of cobalt fed to first oxo reactor.
(2) Percent accountable cobalt at the end of the test based on cobalt in the system at the beginning of the test plus the make-up cobalt.
(3) In weight percent.
(4) Not detectable by EDTA analysis; <5 ppm.

A sample of the aqueous phase from the stripper unit was further stripped with nitrogen after acidification with sulfuric acid. The cobalt concentration did not decrease, showing that no volatile cobalt was present in this phase.

I claim:

1. The method for removing cobalt values from the crude product of a cobalt-catalyzed hydroformylation reaction, said crude product containing cobalt compounds in addition to an organic hydroformylation reaction product, which comprises: (a) contacting said crude product with a stream of stripping gas in the presence of water or aqueous acid at a temperature of not greater than 100? C. and at a pressure below 10 atmospheres, said pressure being lower than the decomposition pressure of said cobalt compounds at said contacting temperature, to entrain volatile cobalt compounds in said stripping gas and to form an aqueous phase containing cobalt values dissolved therein; and (b) separating said aqueous phase from said organic hydroformylation reaction product.

2. A method according to claim 1, wherein the stripping gas containing the volatile cobalt compounds is subsequently contacted with liquid olefin to dissolve said cobalt compounds therein, and the cobaltcontaining olefin is used as feed for the hydroformylation reaction.

3. A method according to claim 1 wherein the organic hydroformylation reaction product from which said aqueous phase has been separated is subjected to a water wash treatment to remove residual cobalt values remaining therein.

4. A method according to claim 3, wherein wash water from said treatment is introduced into the crude hydroformylation reaction product prior to contacting the same with said stripping gas.

5. A method according to claim 1 wherein said contacting is performed in the presence of an aqueous organic acid, the resulting cobalt-containing aqueous phase is concentrated and the concentrate introduced into a zone where said hydroformylation reaction is carried out.

6. A method according to claim 5 wherein the concentrate contains from 1 to 2 wt. % of cobalt (calculated as metallic colbalt).

7. A method according to claim 5 wherein, prior to concentration, said aqueous phase is oxidized with a molecular oxygen-containing gas to destroy volatile cobalt carbonyl species contained therein.

8. A method according to claim 1 wherein said contacting is performed in the presence of water or an aqueous organic acid, the resulting cobalt-containing aqueous phase is concentrated and the concentrate is delivered to a catalyst preforming zone and combined with a slurry of cobalt oxide in higher alcohol and/or a solution of cobalt soap in higher alcohol, and the combination is thereafter introduced into the crude hydroformylation product prior to said stripping stage.

9. A method according to claim 5 wherein the concentrate contains from 1 to 2 wt. % of cobalt (calculated as metallic cobalt).

10. A method according to claim 8 wherein, prior to concentration, said aqueous phase is oxidised with a gas comprising molecular oxygen to destroy volatile cobalt carbonyl species contained therein.

11. A method according to claim 1 wherein the crude product contains from 5 to 15 wt. % of water or aqueous acid based on the organic content of the crude product.

12. A method according to claim 1 wherein the aqueous acid is formic acid.

13. A method according to claim 12, wherein the aqueous acid is 1 to 2 wt. % aqueous formic acid.

14. A method according to claim 1 wherein the stripping gas is used in a stripping gas: crude product volume: volume ratio of from 20:1 to 250:1, as determined at the temperature and pressure used in said contacting step(a).

15. A method according to claim 14, wherein the volume ratio is from 50:1 to 125:1.

16. A method according to claim 12 wherein the stripping gas is selected from synthesis gas, nitrogen and mixtures thereof.

17. A method according to claim 1 wherein said contacting is carried out at a pressure of from 1 to 5 atmospheres absolute.

18. A method according to claim 1, wherein contacting temperature is from 60° to 100° C.

19. A method according to claim 1 wherein the olefinic feedstock is selected from olefins of carbon number 6 to 12 and mixtures of two or more such olefins.

20. A method for producing higher aldehydes and higher alcohols which comprises:
(a) hydroformylating an olefinic feddstock with synthesis gas in the presence of a cobalt-containing catalyst to form a product mixture containing higher aldehyde, higher alcohol, secondary products and dissolved cobalt catalysts;
(b) removing said cobalt catalysts from said product mixture by contacting said product mixture at a temperature of from 60° to 100° C. with a stream of stripping gas comprising carbon monoxide and hydrogen at a pressure below 10 atmospheres in the presence of an aqueous acid to entrain volatile cobalt compounds in said gas and to form an aqueous phase containing cobalt values dissolved therein;
(c) separating said aqueous phase from said aldehyde and said alcohol and recovering said aldehyde and alcohol as hydroformylation reaction product;
(d) recovering the stripping gas containing said volatile cobalt compounds and contacting said recovered gas with said liquid olefinic feedstock to dissolve said cobalt compounds therein; and
(f) recycling said contacted liquid olefinic feedstock to said hydroformylation step (a).

21. A method according to claim 20 wherein said separated aqueous phase is treated to concentrate the cobalt content thereof and said cobalt-containing aqueous concentrate is recycled to said hydroformylation step (a).

22. A method according to claim 20 wherein said separate aqueous phase is treated to concentrate the cobalt content thereof and said cobalt-containing aqueous concentrate is recycled to step (b).

* * * * *